(12) United States Patent
Binder et al.

(10) Patent No.: US 8,080,274 B2
(45) Date of Patent: Dec. 20, 2011

(54) DRY CORN MILL AS A BIOMASS FACTORY

(75) Inventors: Thomas P. Binder, Decatur, IL (US); Thomas V. Gottemoller, Mount Zion, IL (US)

(73) Assignee: Archer Daniels Midland Company, Decatur, IL (US)

( * ) Notice: Subject to any disclaimer, the term of this patent is extended or adjusted under 35 U.S.C. 154(b) by 646 days.

(21) Appl. No.: 12/037,316

(22) Filed: Feb. 26, 2008

(65) Prior Publication Data

US 2008/0213429 A1 Sep. 4, 2008

Related U.S. Application Data

(60) Provisional application No. 60/904,527, filed on Mar. 2, 2007.

(51) Int. Cl.
*A23L 1/00* (2006.01)
(52) U.S. Cl. .......... 426/618; 426/622; 426/656; 426/49; 435/167
(58) Field of Classification Search .................. None
See application file for complete search history.

(56) References Cited

U.S. PATENT DOCUMENTS

| | | | | |
|---|---|---|---|---|
| 2,879,167 | A * | 3/1959 | Grandel | 426/457 |
| 4,495,207 | A | 1/1985 | Christianson et al. | |
| 4,710,300 | A * | 12/1987 | Kristoufek | 210/603 |
| 4,737,371 | A * | 4/1988 | Bookwalter | 426/462 |
| 5,250,313 | A | 10/1993 | Gigure | |
| 5,843,499 | A | 12/1998 | Moreau et al. | |
| 2005/0118692 | A1* | 6/2005 | Kinley et al. | 435/161 |
| 2005/0153410 | A1* | 7/2005 | Hallberg et al. | 435/161 |
| 2005/0252858 | A1 | 11/2005 | Peyton et al. | |
| 2006/0029715 | A1 | 2/2006 | Cheryan | |
| 2006/0177551 | A1* | 8/2006 | Van Thorre | 426/489 |
| 2006/0251764 | A1* | 11/2006 | Abbas et al. | 426/53 |
| 2007/0178567 | A1* | 8/2007 | Lewis | 435/161 |
| 2007/0264413 | A1 | 11/2007 | Binder et al. | |

OTHER PUBLICATIONS

Gollakota et al. Biogas (Natural Gas?) Production by Anaerobic Digestion of OII Cake by a Mixed Culture Isolated from Cow Dung, Jan. 14, 1983, Biochemical and Biophysical Research Communications, vol. 110 No. 1 pp. 32-35.*
Wahjudi, J., et al, Quick Fiber Process: Effect of Mash Temperature, Dry Solids, and Residual Germ on Fiber Yield and Purity, Cereal Chem. 77(5) : 640-644 (2000).
Taylor, F., et al., Fuel Ethanol Fermentation of Degermed and Dehullled Corn, USDA, Eastern Regional Research Center, Wyndoor, PA 19038.
Ferrell, John, "Federal Goals for Biorefinery Development and Implications for Fuel and Power in California" Mar. 1, 2005.
Dien, et al., 'Fermentation of "Quick Fiber" Produced from a Modified Corn-Milling Process into Ethanol and Recovery of Corn Fiber Oil', Applied Biochemistry and Biotechnology, 2004 vol. 113-116, pp. 937-939.
Singh, V. et al., "Modified Dry Grind Ethanol Process" Publication of Agricultural Engineering Department, University of Illinois at Urbana-Champaign, Jul. 18, 2001.

* cited by examiner

*Primary Examiner* — Humera Sheikh
*Assistant Examiner* — Felicia King
(74) *Attorney, Agent, or Firm* — Mark W. Roberts

(57) ABSTRACT

Novel grain products are disclosed. Modified de-oiled distillers dried grains that include stillage obtained from anaerobic digestion of the oil cake are provided. In various embodiments, the modified de-oiled distillers dried grains may be the stillage from anaerobic digestion of the oil cake only, may also include the ordinary DDGs obtained from fermentation of the endosperm portion of the grain, or may include stillage obtained from further anaerobic digestion of the ordinary DDGs.

3 Claims, 4 Drawing Sheets

A schematic of the conventional dry grind ethanol process.

Figure 1    A schematic of the conventional dry grind ethanol process.

Figure 2   A schematic of the modified dry grind ethanol process with germ and fiber recovery.

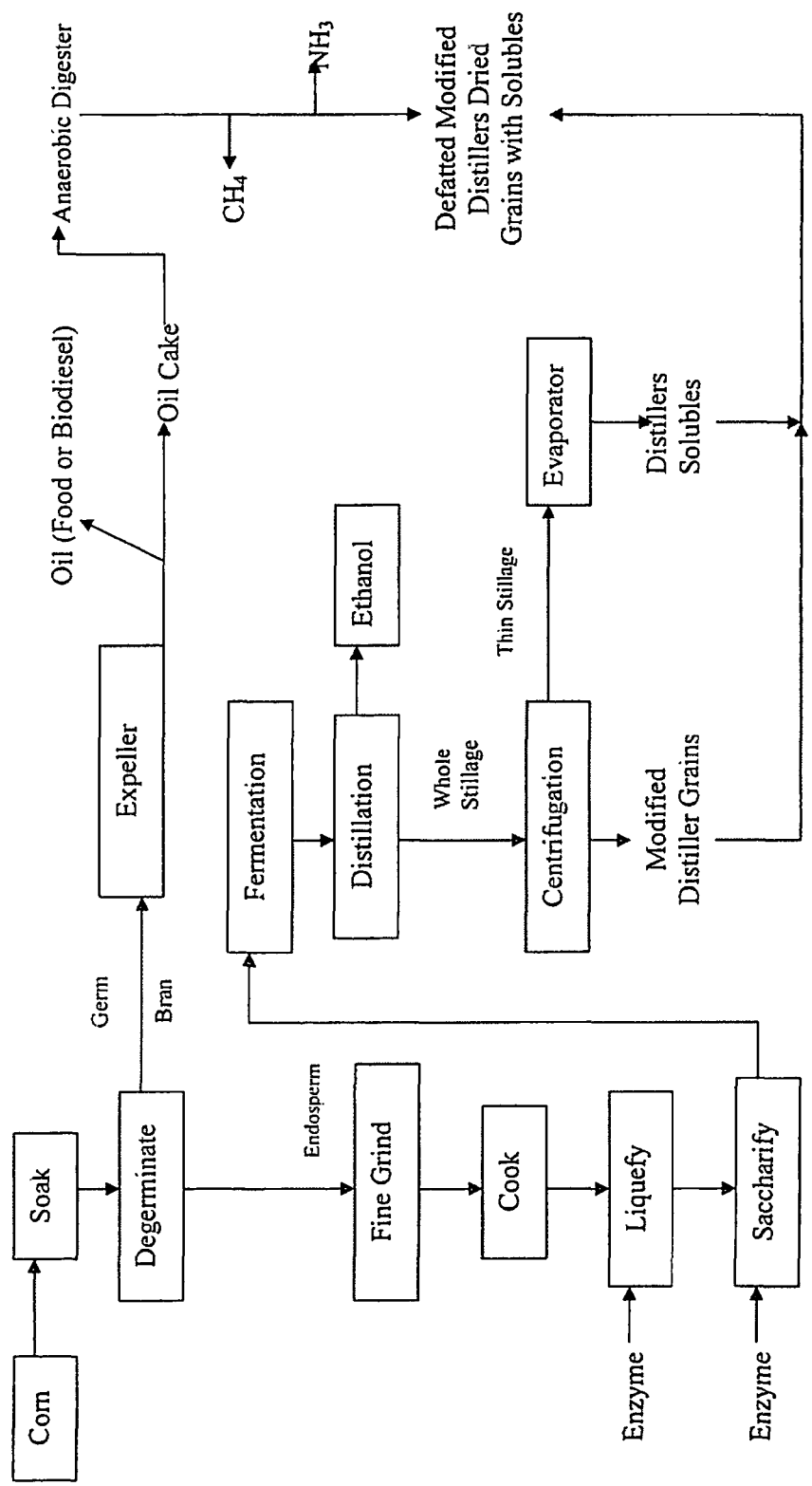

DRY CORN MILL AS A BIOMASS FACTORY

CROSS-REFERENCE TO RELATED APPLICATION

This application is a utility application and claims the benefit of priority to U.S. Provisional Patent Application Ser. No. 60/904,527, filed on Mar. 2, 2007. The entire contents of U.S. Provisional Patent Application Ser. No. 60/904,527 is incorporated by reference into this utility patent application.

BACKGROUND OF THE INVENTION

The following includes information that may be useful in understanding the present teachings. It is not an admission that any of the information provided herein is prior art, or material, to the presently described or claimed inventions, or that any publication or document that is specifically or implicitly referenced is prior art.

1. Field of the Invention

The present teachings relate to, but are not limited to, the field of corn product production. The invention relates, for example, to de-oiled flour and production of methane, ammonia, and modified dried distillers grains as well as modified dry grind ethanol processes for their production.

2. Description of the Background Art

Corn oil has a number of properties and uses that are attractive to consumers and to producers of consumer products. Refined corn oil is crude corn oil from which fatty acids and phospholipids have been removed. Refined corn oil is reputed to have excellent frying quality and resist smoking and/or discoloration. Refined corn oil typically has a pleasant taste, resists development of off-flavors, and has a high polyunsaturated fat content. Refined corn oil has also been postulated to reduce blood cholesterol levels. Products such as margarines, salad oils, and cooking oils may include refined corn oil. Corn oil may also be used for biodiesel applications.

Corn processing methods may be divided into a number of broad groups, including dry grind ethanol, modified dry grind ethanol, corn wet milling and corn dry milling (Singh, V., et al., "Modified Dry Grind Ethanol Process," Publication of the Agricultural Engineering Dept. of Univ. of Ill. and Urbana-Champaign, UILU No. 2001-7021, Jul. 18, 2001, incorporated by reference herein). Variation within processes may occur based on the preferences of the miller.

In a typical traditional dry grind ethanol operation, whole corn is ground, treated with enzymes, and cooked. The resulting "mash" is treated with enzymes to further liberate glucose from the starchy endosperm tissue. The converted mash is fermented and distilled, producing ethanol, carbon dioxide, and distillers dried grains (DDGs), which are the undissolved solid components (stillage) remaining in the fermentation tank after the broth is removed. These conventional DDGs are thus comprised of yeast and unfermented left over components of the corn.

Traditional dry grind ethanol operations have a number of disadvantages. For instance, use of the entire kernel in the mash, including the non-starch portions of the kernel, reduces the efficiency of the operation. Furthermore, the non-ethanol byproducts (including DDGs) have a relatively low value, and they include a high oil content that is relatively difficult to remove. A typical conventional dry grind ethanol operation is depicted in FIG. 1.

In a typical modified dry grind ethanol operation, corn is first cleaned in a dry state, to remove cobs and other undesirable components, such as iron or stones. The corn may also be wet-cleaned to remove dirt or dust. Following cleaning, the corn is tempered to between about 14% and 22% moisture, typically about 20% moisture. Tempering entails treating the corn with cold water, hot water, and/or steam. This softens the bran and germ and allows them to be more easily separated from the endosperm.

Following tempering, and while the corn is still moist, the germ, tip cap, and pericarp (bran) are separated from the endosperm, which is customarily used to make grits, meals, and flours. The bran and germ proceed through the "through stock" stream, which is dried, cooked, and aspirated. This removes the bran. The remaining dried germ, which typically contains about 45% corn oil on a dry basis, is transferred to a separate facility, where the oil is removed through chemical extraction or auger press/expeller. The corn residue from the press or extraction (oil cake) is then used as an animal feed.

The non-bran, non-germ components of the kernel (principally endosperm tissue) are ground and converted to mash, as is done in the conventional dry grind ethanol operation. Again, the mash is typically treated with enzymes to liberate glucose. The mash (more accurately the glucose in the mash) is fermented and distilled, producing ethanol, DDGs and carbon dioxide. Because the germ, which contains the highest oil content of the corn grain is not used in the fermentation process, the DDGs from this modified process may be considered de-oiled relative to the DDG's obtained from the ordinary process A typical modified dry grind ethanol process is shown in FIG. 2.

Modified dry grind ethanol operations are typically more advantageous than conventional dry grind ethanol operations, because the additional capital cost involved in establishing modified operations is offset by the added value obtained by separating the germ and bran from the materials used in fermentations. The separated germ may be shipped to a treatment facility, then extracted or treated with an expeller to obtain corn oil and the remaining oil cake is customarily used as an animal feed component.

Corn dry milling, without ethanol production, typically involves addition of water to the corn kernel, increasing the moisture content to about 22%. Germ is made more resilient by the addition of water due to differential swelling relative to the other kernel components. The corn is treated (by abrasion or grinding) to break the kernel into bran, germ, and endosperm fragments, and the pericarp and germ fragments are removed from the endosperm. Because the separation is not highly specific, the germ fraction from corn dry milling includes a lower corn oil concentration than the germ fraction from a modified dry grind ethanol operation. Therefore, the germ and bran fractions are usually sold as ingredients in animal foods. The germ and bran fractions are typically not incorporated into any whole corn products, because the amount of oil that is present may be sufficient to foul the product. Following removal of the germ fraction and the bran fraction, the endosperm fraction is separated based on size of the various flakes Endosperm products include flaking grits, brewers grits, cones, meal, and flour. A typical dry corn milling process is shown in FIG. 3.

It would be desirable to provide an improved dry corn milling process to extract further value from corn and similar grains. It would further be desirable to produce an improved de-oiled DDGs and other de-oiled whole grain products that may be made from such an improved process.

SUMMARY OF THE INVENTION

The inventions described and claimed herein have many attributes and encompass many embodiments including, but not limited to, those set forth in this Summary. The inventions described and claimed herein are not limited to or by the features or embodiments identified in this Summary, which is included for purposes of illustration only and not restriction.

A modified de-oiled distillers dried grain product and process for making the same is disclosed herein. The modified de-oiled distillers dried grain product includes oil in an amount (by volume) selected from less than about 20%, less than about 15%, less than about 10%, less than about 5%, or less than about 1% of that of de-oiled distillers dried grain not made by the process described herein. In one aspect, the modified DDGs are characterized by including not only the stillage from fermenting the endosperm portion of a the grain, but also includes stillage obtained from treating the oil cake residue obtained from expelling oil from the germ of the grain to an anaerobic digestion process.

In one illustrative aspect, a method for producing a modified de-oiled distillers dried grain product in a modified dry grind ethanol process is taught. Such a method, for example, includes (a) providing a grain;
(b) soaking the grain in water to produce a moisturized grain;
(c) degerminating the moisturized grain to produce a stream of germ and bran (pericarp) and an endosperm stream;
(d) grinding the endosperm stream;
(e) cooking the endosperm stream;
(f) liquefying the endosperm stream;
(g) saccharifying the endosperm stream;
(h) fermenting the endosperm stream;
(i) distilling the endosperm stream to produce ethanol and whole stillage;
(j) removing ethanol;
(k) treating the whole stillage in an anaerobic digester, producing methane and ammonia.
(l) extracting oil from the germ/bran stream to produce oil and an oil cake;
(m) removing the oil;
(n) treating the oil cake in an anaerobic digester with the whole stillage in step (k), producing methane, ammonia, and a digested oil cake;
(o) removing the methane;
(p) removing the ammonia; and
(q) combining the digested oil cake, the modified distillers grains, and the distillers solubles to produce a modified de-oiled distillers dried grains product.

In one illustrative embodiment, a method for producing a modified de-oiled distillers dried grains product in a modified dry grind ethanol process is disclosed that includes the step of treating an oil cake in an anaerobic digester to produce methane, ammonia and a spent oil cake. Modified de-oiled distillers dried grain products produced by the methods disclosed herein may be used, for example, as added-value animal feed.

Extracting steps discussed herein may be performed, for example, using chemical extraction, expeller extraction, hydraulic press extraction, carbon dioxide-assisted extraction, and supercritical fluid extraction. Expeller extraction is preferred. Where supercritical fluid extraction is used, a preferred supercritical fluid is carbon dioxide with or without co-solvents such as propane and/or ethanol. Suitable methods of supercritical fluid extraction are set forth, for example, in U.S. Pat. No. 4,495,207, to Christianson, et al., which is incorporated by reference herein.

Grains or grain-like raw materials for use with the teachings herein may include, for example, but are not limited to, wheat, millet, barley, sorghum, triticale, rice, corn, amaranth, buckwheat, and quinoa. Corn is preferred. No particular strain of corn is required.

BRIEF DESCRIPTION OF THE DRAWINGS

FIG. 4. depicts an inventive process for the production of modified de-oiled DDG.

DETAILED DESCRIPTION OF THE INVENTION

I. Definitions

Figure 1:
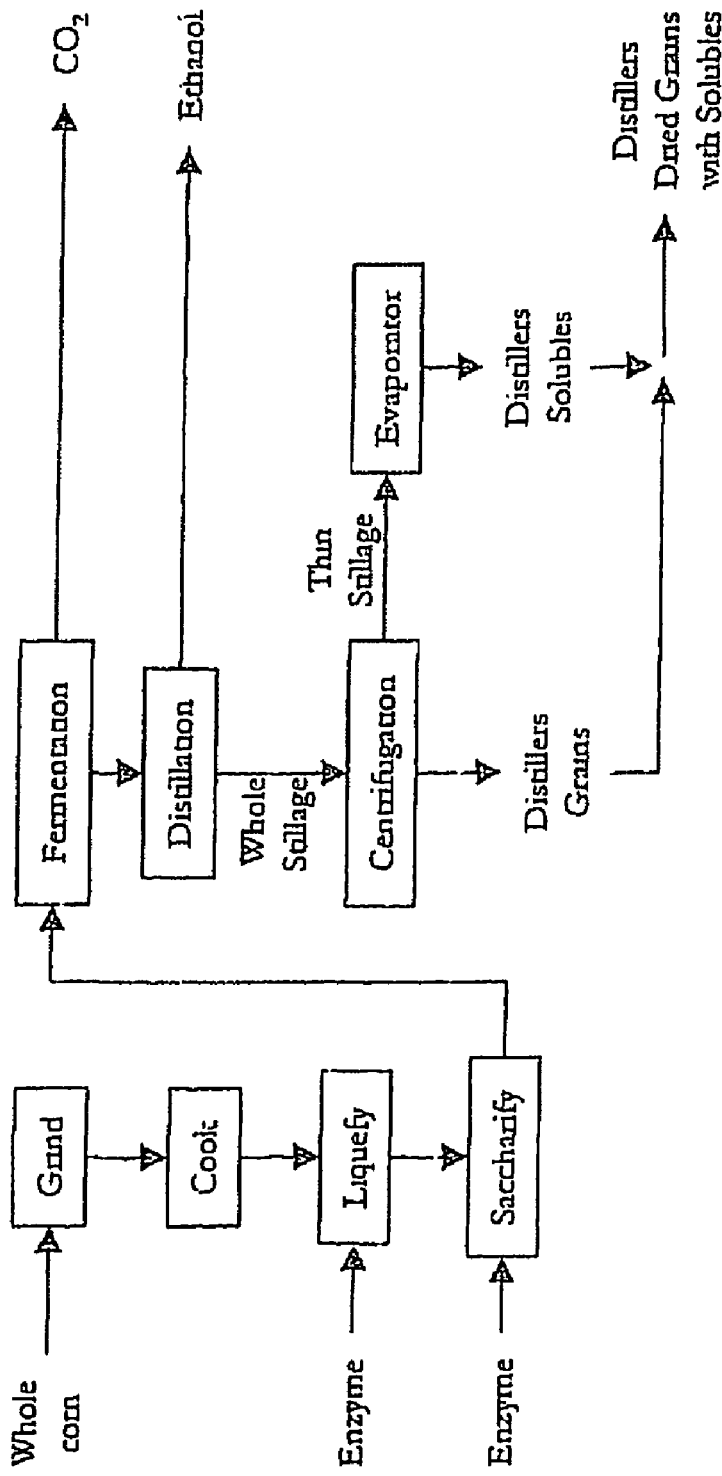
FIG. 1. depicts a conventional dry mill ethanol production process, (Singh, et al.).
Figure 2:
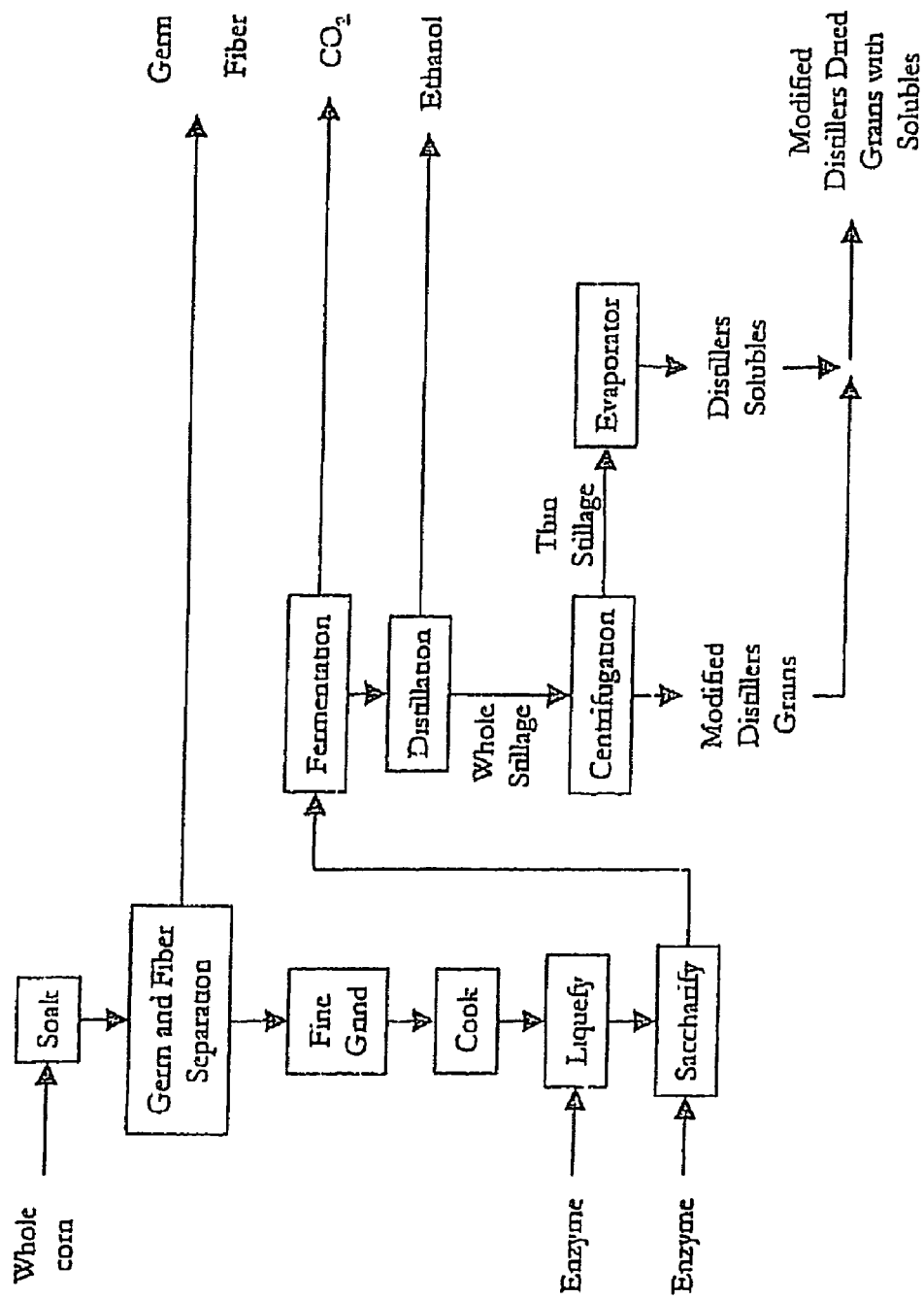
FIG. 2. depicts a modified dry mill ethanol production process (Singh, et al.).
Figure 3:
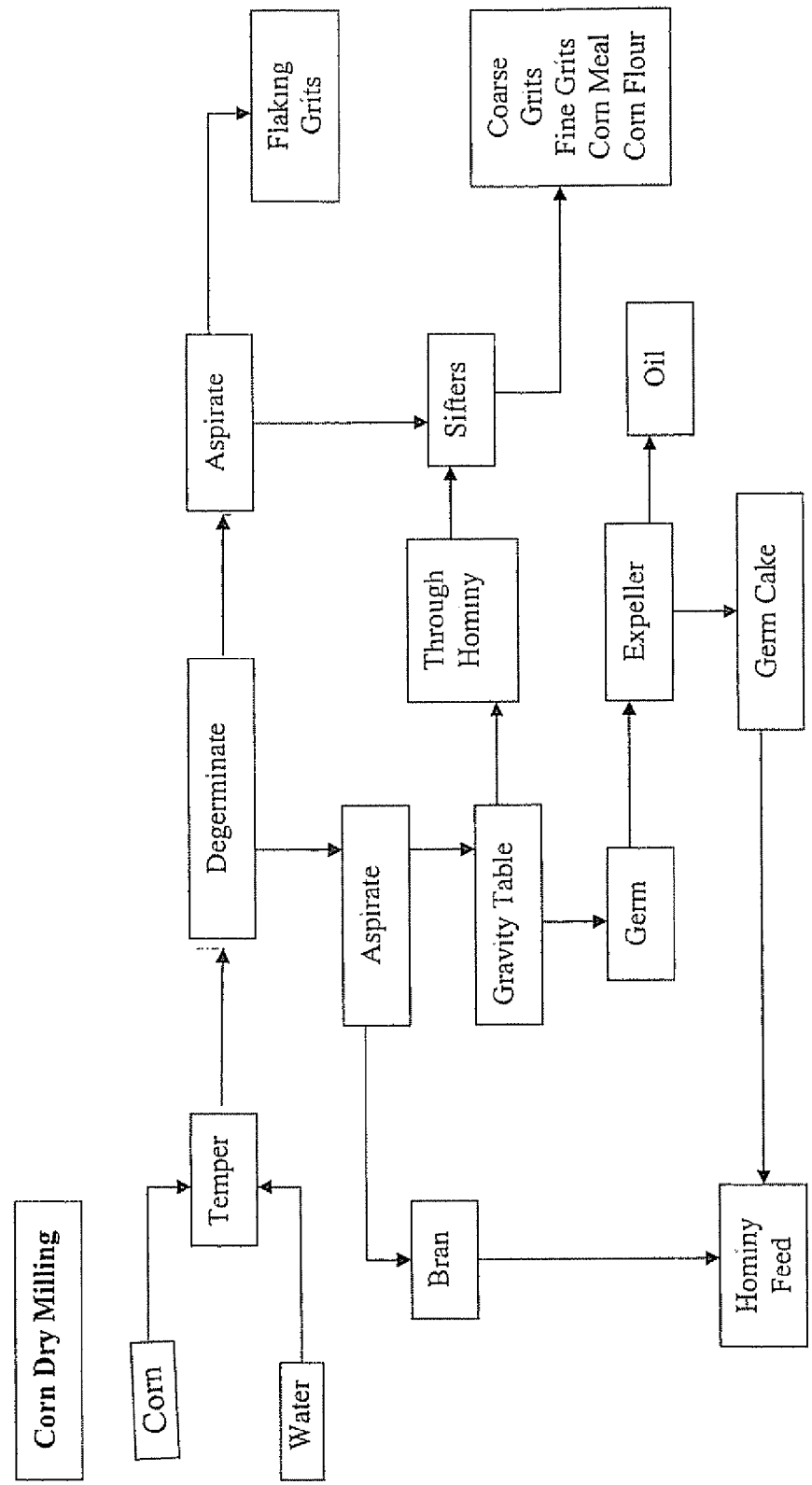
FIG. 3. depicts a conventional dry mill corn milling process. (Iowa Corn Growers).

To provide a clear and consistent understanding of the specification and claims, including the scope to be given to terms therein, the following definitions are provided. Note that the term "a" or "an" entity refers to one or more of that entity unless otherwise noted. As such, the terms "a," "an," "one or more," and "at least one" can be used interchangeably herein.

As used herein, "de-oiled" means that a product contains less oil than the product would otherwise have contained had oil not been removed at some point during the production of the product.

As used herein, "distillers dried grains" or "DDS" means that product obtained after the removal of ethyl alcohol by distillation from the yeast fermentation of a grain or a grain mixture by separating the resultant coarse grain faction of the whole stillage and drying it by methods known by those skilled in the grain distilling arts.

As used herein, "grain products" includes but is not limited to at least one of grits, flours, cones, meals, and flakes. "Products" preceded by a specific grain, i.e., "corn products," includes but is not limited to grits, flours, cones, meals and flakes made from that grain.

II. Discussion

Discussion of the methods and compositions taught herein will be made using corn as an exemplary grain for the practice of the invention. Those skilled in the art will, with the benefit of this disclosure, recognize that the methods and compositions may be practiced with other grains and grain-like substances, as discussed herein. Grains or grain-like raw materials for use with the teachings herein may include, for example, but are not limited to, wheat, millet, barley, sorghum, triticale, rice, corn, amaranth, buckwheat, and quinoa. Corn is preferred. No particular strain of corn is required.

A. Modified De-Oiled Distillers Dried Grains and Processes for their Preparation A modified dry grind ethanol process is an effective way to produce ethanol. The process also results in the production of DDG. Although DDG may be sold as an animal feed, it would be desirable to obtain a higher value stream from the by-products of the ethanol production.

We have found that multiple high value streams that can be obtained as by-product of ethanol production include corn oil, methane, and ammonia. This corn oil may be obtained, for example, by extracting oil from the wet germ stream that is produced. Methane and ammonia may be obtained by treating an oil cake and whole stillage in an anaerobic digester. In other embodiments, the ordinary DDGs obtained from fermentation of the endosperm portion of the grain are also further treated in an anaerobic digester. In some embodiments the treatment of the ordinary DDGs and oil-cake in the anaerobic digester are performed simultaneously. In other embodiments the anaerobic digestion of these components are performed separately and the stillage from the anaerobic-digestions are combined.

Obtaining these by-products also has the salutary effect of producing a modified de-oiled DDG which includes a digested oil cake and whole stillage. This DDG may have advantageous nutritional properties for certain livestock. It may also be less susceptible to spoilage. A modified de-oiled distillers dried grain product may include oil in an amount (by volume) selected from less than about 20%, less than about 15%, less than about 10%, less than about 5%, less than about 2%, less than about 1%, or between about 1% to about 2% of that of de-oiled distillers dried grains not treated by anaerobic digestion of the oil cake.

One exemplary method of obtaining oil from a modified dry grind ethanol process, for example, includes the following steps, though those skilled in the art will recognize that some steps may be added or deleted without affecting the nature of the invention:

(a) providing corn;
(b) soaking the corn in water to produce a moisturized corn;
(c) degerminating the moisturized corn to produce a stream of germ and bran (pericarp) and an endosperm stream;
(d) grinding the endosperm stream;
(e) cooking the endosperm stream;
(f) liquefying the endosperm stream;
(g) saccharifying the endosperm stream;
(h) fermenting the endosperm stream;
(i) distilling the endosperm stream to produce ethanol and whole stillage;
(j) adding the whole stillage to an anaerobic digester, producing methane, and ammonia;
(k) extracting oil from the germ/bran stream to produce oil and an oil cake;
(l) treating the full or partially de-oiled oil cake in an anaerobic digester in the same anaerobic digester above, producing methane, ammonia, and digested oil cake;
(m) removing the methane; and
(n) removing the ammonia.

In a further aspect, a method for producing a modified de-oiled distillers dried grains product in a modified dry grind ethanol process is provided that includes the step of extracting a germ stream or a germ and bran stream to produce oil and an oil cake, then treating said oil cake in an anaerobic digester. Modified de-oiled distillers dried grain products produced by the methods disclosed herein may be used, for example, as added-value animal feed. It may be used as a designer co-product in animal feeds (including as a by-pass protein) and/or pet foods. In particular, it may be valuable as a soy fiber (oligosaccharide) substitute in pet foods, particularly in pet foods for geriatric use. It may also be used as a blend with crude glycerin from soy biodiesel production.

Extracting steps discussed herein may be performed, for example, using chemical extraction, expeller extraction (with or without carbon dioxide and co-solvents addition), a hydraulic or mechanical press, and supercritical fluid extraction. Expeller extraction is preferred. Where supercritical fluid extraction is used, a preferred supercritical fluid is carbon dioxide with or without co-solvents. Use of an expeller in extraction is preferred. Although it is not critical, ideally the extraction will be conducted at or near the mill and the expeller operation may be followed with extraction with a solvent such as mixed hexanes.

Anaerobic digestion may be performed, for instance in batch or continuous anaerobic digesters which can range in capacities from 10,000 gallons of feed per day up to 10,000,000 gallons of feed per day. Examples of companies supplying anaerobic digesters, also known as bioreactors, include Babcock & Wilcox, Biothane Systems, Ely Energy and Recovered Energy Resources. A modified de-oiled DDG as taught herein may comprise about 25 to about 30% protein, about 1 to about 2% oil, about 14 to about 17% ash, about 30 to about 50% fiber, and about 5 to about 15% carbohydrate. Generally one would expect to remove about 0.2-1.0 cubic feet of methane per pound of Biological Oxygen Demand (BOD). About 1-2% of the corn brought into the plant would be recovered as ammonia, and about 5-25% of the corn brought into the plant would be recovered as modified DDG.

III. EXAMPLES

The examples below are only representative of some aspects of the invention. It will be understood by those skilled in the art that the invention as set forth in the specification can be practiced with a variety of microorganisms and promoters. These examples should not be interpreted as limiting the invention in any way not explicitly stated in the claims.

Example 1

Example 1 describes a prophetic example. Whole U.S. No. 2 corn is dry cleaned by passing over magnets to remove iron, then aspirated though a Kice aspirator to remove dust, fines and remaining cob. The corn is wet cleaned to remove residual dust and other filth and the moisture content is adjusted to about 20%. The corn after tempering has the bran, pericarp and germ abraded away in a degerminator. For example a Beall degerminator is used. Most of any bran or germ that sticks with the endosperm is removed then through aspirator and gravity tables.

The germ/bran/pericarp fraction is then dried and the oil is removed with the use of an expeller. For example, a DeSmet Rosedown expeller press with the oil removed further from the cake by extraction with a mixtures of hexanes through a Crown Model III extractor may be used.

The endosperm is ground though hammer mills to allow the particles to hydrate for cooking and enzyme conversion by alpha amylase and gluco-amylase. These enzymes may be supplied by, for example, Genecor or Novozymes. Once the fermentation is complete (to a level deemed satisfactory by one skilled in the art), the ethanol is removed, leaving whole stillage. Ethanol is removed using a still.

The stillage and de-oil germ are then sent to an anaerobic digester. For example, a Biothane anaerobic digester may be used. Methane is collected off the digester unit. The treated liquid is then moved forward and the ammonia is steam stripped from the treated liquid. The liquid is then evaporated and dried for use as a modified de-oiled germ for animal feed. In certain embodiments, the solubles in the liquid may be recovered separately and added back to the modified de-oiled DDG product. The modified de-oiled DDG comprises about 25 to about 30% protein, about 1 to about 2% oil, about 14 to about 17% ash, about 30 to about 50% fiber, and about 5 to about 15% carbohydrates.

Patents, patent applications, publications, scientific articles, books, web sites, and other documents and materials referenced or mentioned herein are indicative of the levels of skill of those skilled in the art to which the inventions pertain, as of the date each publication was written, and all are incorporated by reference as if fully rewritten herein. Additionally, all claims in this application, and all priority applications, including but not limited to original claims, are hereby incorporated in their entirety into, and form a part of the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above including but not limited to any original claims.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

We claim:

1. A modified de-oiled distillers dried grain product comprising stillage obtained from, a fermentation of an endosperm containing a portion of a grain combined with stillage obtained from b anaerobic digestion of an oil cake residue wherein the residue is obtained by c removing a portion of oil from germ obtained from the grain, wherein the modified de-oiled distillers dried grain product comprises about 25 to about 30% protein, about 1 to about 2% oil, about 14 to about 17% ash, about 30 to about 50% fiber, and about 5 to about 15% carbohydrates.

2. A modified distillers dried grain product of claim 1, wherein said de-oiled distillers dried grain product is derived from corn.

3. The modified de-oiled distillers dried grain product of claim 1 comprising 28% protein, 2% oil, 15% ash, 45% fiber, and 10% carbohydrates.

\* \* \* \* \*